United States Patent [19]

Schuetz

[11] 4,047,891

[45] Sept. 13, 1977

[54] DENSITY CONTROL SYSTEM

[75] Inventor: Adolph August Schuetz, East Hampton, Conn.

[73] Assignee: Combustion Engineering, Inc., Windsor, Conn.

[21] Appl. No.: 671,199

[22] Filed: Apr. 21, 1976

[51] Int. Cl.² ............... C01B 17/58; B01J 10/00; G01N 9/26; G01N 9/36
[52] U.S. Cl. ............... 23/230 A; 23/253 A; 23/284; 73/32 R; 55/84; 423/242
[58] Field of Search ............... 23/230 A, 253 A, 284, 23/260, 285; 73/32 R; 55/84, 85, DIG. 30, 257 C; 423/242

[56] References Cited

U.S. PATENT DOCUMENTS

| | | | |
|---|---|---|---|
| 3,433,057 | 3/1969 | Halsey | 73/32 X |
| 3,897,540 | 7/1975 | Onnen | 23/230 A |
| 3,904,370 | 9/1975 | Robison | 23/230 A |
| 3,989,465 | 11/1976 | Onnen | 23/253 A |

Primary Examiner—R.E. Serwin
Attorney, Agent, or Firm—Arthur L. Wade

[57] ABSTRACT

An air quality control system scrubs flue gas of $SO_2$ and particulates with a slurry of lime/limestone and water. The system includes a tank below the contact of gas and slurry in which the chemical action is completed and from which the slurry is recirculated to the scrubber. A bubbler system is connected to the reaction tank to detect the density of the slurry and monitor or control the density. The bubbler system is supplied the liquid and dissolved solids decanted from the thickener to which the slurry is drawn for disposal.

5 Claims, 2 Drawing Figures

DENSITY CONTROL SYSTEM

BACKGROUND OF THE INVENTION

1. Field of the Invention:

The present invention relates to the corrected measurement of the amount of finely divided solids suspended in liquid to form a slurry. More specifically, the invention relates to compensating the measurement for the variations in solids dissolved in the liquid component of the slurry.

2. Description of the Prior Art:

Governmental agencies are placing stringent emission limitations on oil and coal-fired combustion equipment. At this point in time the U.S. Government is demanding 1.2 lbs. $SO_2/10^6$ BTU heat input. Lime/limestone is generally selected for scrubbing systems although they yield no salable chemical by-product.

There are two general approaches to bringing an additive with a large percentage of calcium into effective contact with the combustion compounds. The first is furnace injection. The additive is injected into the furnace of a steam generating unit where it is calcined and reacts with $SO_2$ and $SO_3$ to form compounds of calcium. The second is the tail-end and differs from the furnace injection in the technique for introducing the additives.

In the tail-end system, the additive, a slurry of pulverized limestone or slaked lime, is injected into the scrubber through which flue gas is passed. A contact bed is mounted in the scrubber. Spray nozzles for the slurry are mounted under the bed. The gas, laden with $SO_2$ and particulate matter enters the bed where it is brought into contact with the slurry sprayed from the nozzles into the bed. The reacted materials drain to the scrubber reaction tank below the bed, the tank providing retention time for completion of chemical reactions and precipitation of solids.

Accurate control of percent solids in the reaction tank is required to avoid scaling. Calcium sulfate scaling takes place when the slurry becomes supersaturated with calcium and sulfate ions. The ions combine and attach to the walls, pots and pipes of the scrubber as crystals.

The mechanism whereby these ions build up in solution to a level of supersaturation is well-known in the art. There are several factors that require controlling to avoid scaling. The factor of present concern is percent solids in the system. The only practical way to go about this measurement is to interpret the percent solids from a density measurement. The bubbler system was selected as dependable in making this measurement.

The adaptation of the bubbler system and application of it to the slurry collected in the reaction tank was seemingly quite simple. The bubbler system of measurement is well-known. In the more simple description of this system, a source of fluid is discharged, below a liquid surface from a fixed elevation, through the open end of a pipe. The pressure of the fluid in the pipe has a measurable relation to the height of the liquid, above the end of the pipe.

If a second pipe discharge is located at a second elevation from that of the first pipe discharge, the differential pressures of the fluids in each pipe will relate to the density of the liquid into which the pipes discharge. However, there is a present problem.

The problem is focused by application of the bubbler system to this measurement of the percent of solids in the slurry with the slurry having dissolved and undissolved constituents in the water. In the instrument responding to the differential pressure, and calibrated in percent solids in the slurry, the dissolved material can introduce a significant error of as much as 30% of full scale. At present, this error has been kept tolerable only by frequent manual calibrations.

Automatic compensation of the measurement is desired.

SUMMARY OF THE INVENTION

It is a principal object of the invention to apply a dual bubbler system to the continuous measurement and control of undissolved solids in a slurry.

It is another object to supply a fluid to the bubbler pipes of a dual bubbler system with a dissolved chemical species compatible with the dissolved chemical species of the slurry measured by the system.

The present invention contemplates a system for providing a slurry of water and slaked lime or limestone which contacts combustion gases for the removal of undesirable impurities before discharge of the gases to the atmosphere. The slurry must have its solids controlled to a predetermined percent and is mechanically flowed into direct contact with the flue gases processed. The density of the solids and water mixture is detected with a dual bubbler system which discharges water from its two pipes into the slurry. The water is selected from a source in the system which contains dissolved solids compatible with the dissolved solids in the water of the slurry. The detection signals are thereby kept representative of the undissolved solids to a predetermined quantity of the slurry.

Other objects, advantages and features of the invention will become apparent to one skilled in the art upon consideration of the written specification, appended claims, and attached drawing, wherein;

FIG. 1 is a somewhat diagrammatic flow diagram of a flue gas scrubber system in which the invention is embodied; and FIG. 2 is a detailed portion of the reaction tank of the FIG. 1 system at which the bubbler system responds to the density of the slurry in the tank.

DESCRIPTION OF THE PREFERRED EMBODIMENT

The development of the lime/limestone scrubber systems started at least as early as 1964. Of course, the very large quantities of fluids treated and treating fluids handled have caused many problems to descend from 1964 to the present. The invention here solves only one of these numerous problems. However, the invention is very important to the success of the system.

Figure 1:
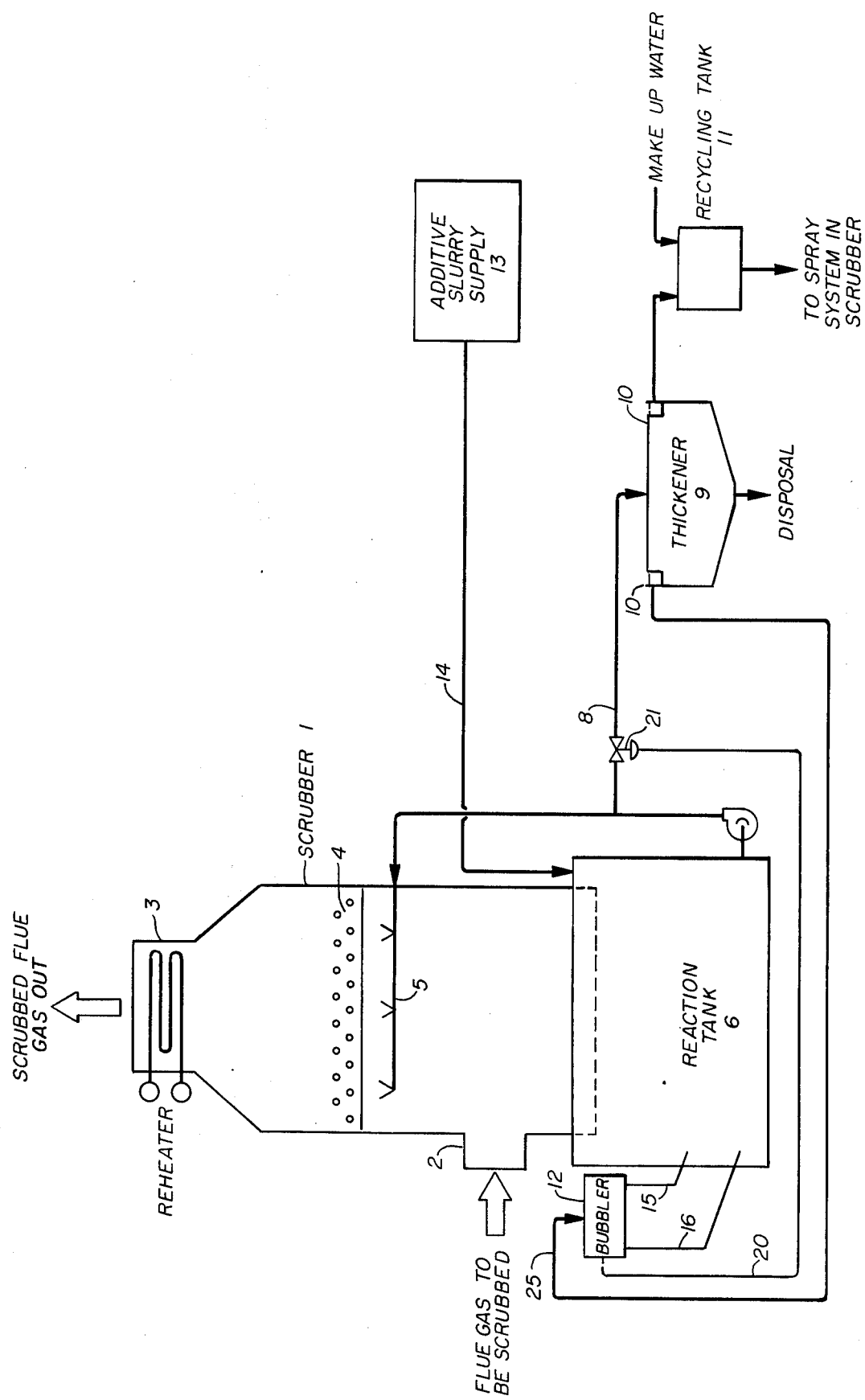
Figure 2:
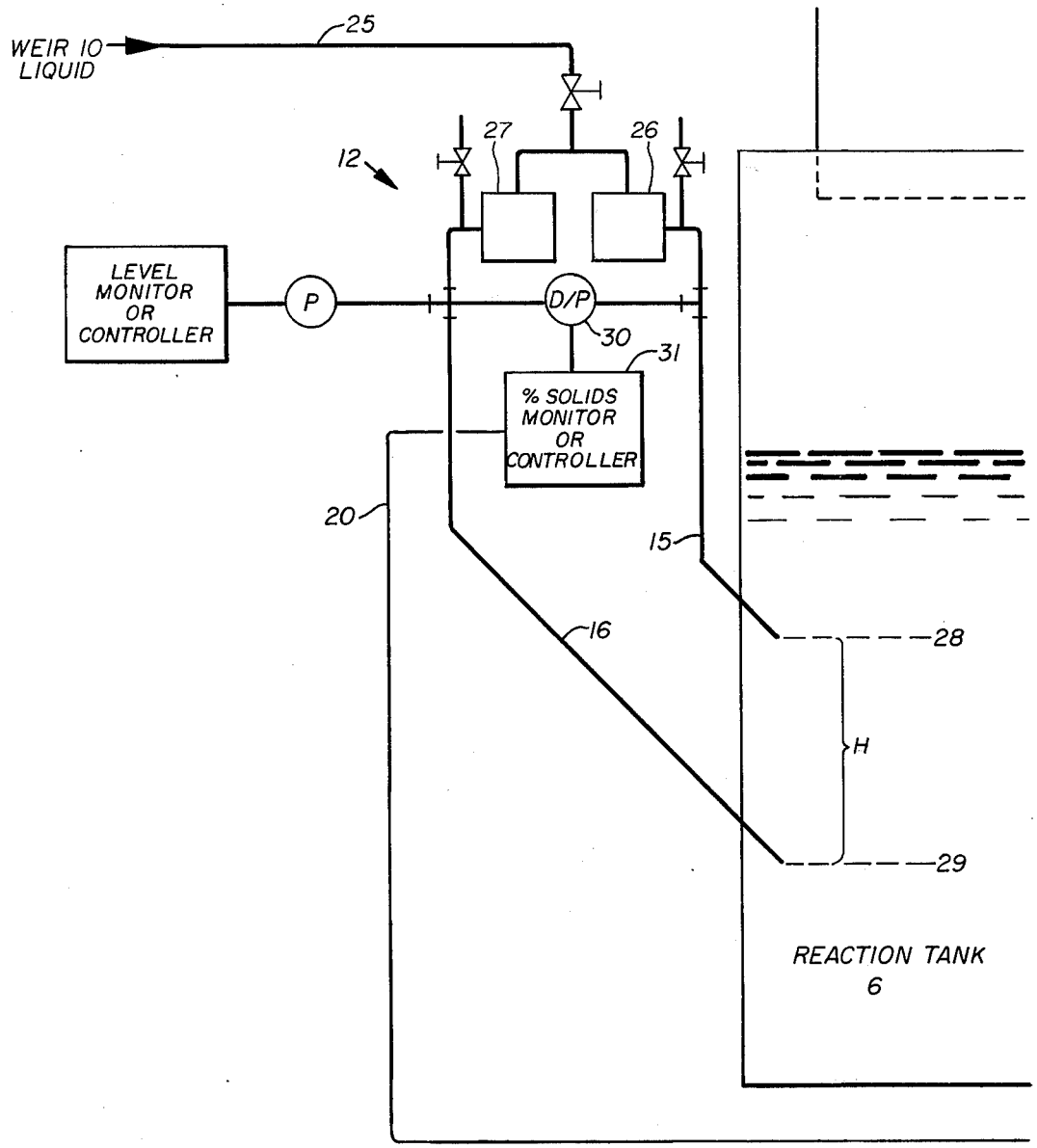

FIG. 1 is only a very general overview of the structure in which the invention is embodied. Only enough detail is shown to clearly teach the invention. In other words, a conscious effort is made to keep the disclosure simple and direct while adequately teaching the invention.

FIG. 1 is dominated by scrubber 1. This is a vertical tower. The gas to be treated, or scrubbed, flows into the bottom inlet 2 and flows out the top of the tower at 3.

The basic scrubbing of the gas is brought about in bed 4. The lime/limestone slurry is sprayed from nozzles 5 up into bed 4 and this material is intimately contacted by the upflowing gas as it passes through the bed 4.

The slurry, having removed the $SO_2$, and other material from the gas, gravities into reaction tank 6. A level of the inventory of the slurry is carried in tank 6. Pump 7 recirculates the slurry to the nozzles 5. A bleed flow line 8 removes a desired amount of the slurry to thickener 9.

In thickener 9 the solids settle and clarified water is available from decanting over weir 10. Part of this decanted water flows to recycling tank 11. It is resprayed back into scrubber 1 (not shown) and part is available to the bubbler system 12. Fresh slurry is available from supply 13 and is inserted into the system through line 14 which extends to reaction tank 6.

The bubbler system 12 extends its two open-ended sensing pipes 15, 16 into tank 6. The signal generated by the differential pressure between the fluids discharged from pipes 15, 16 is used to control the percent solids in the slurry within tank 6. The control is represented here by line 20 placing the generated signal on valve 21 in bleed flow line 8. The basic point of this portion of the disclosure is that a bubbler system is responsive to the density of the slurry in the system, the fluid available to the bubbler system is from the thickener 9 and the bubbler system generates a control signal which regulates the density/percent solids of the slurry.

REVIEW OF FIG. 1

The present invention is embodied in a meter which manifests the percent solids of a slurry of the lime/limestone system which removes certain material from the flue gases of fossil fuel combustion. The successful operation of the system requires accurate percent solids control of the slurry to prevent scale formation.

The slurry of the system disclosed is composed of two major separable constituents. One consists of the water and any dissolved chemical species like calcium, sulfate, sulfite and magnesium ions. The other consists of the undissolved constituents, referred to as the percent solids. As this meter is basically a density measuring device that relates percent solids to density, any variations between the quantities of dissolved chemical species in the bubbler liquid and the slurry liquid will cause the significant error of the problem solved by the present invention.

The present disclosure is not designed to show the entire slurry system and its relationship to a combustion system. There are many problems in operating these systems which move large quantities of undissolved solids in acquiring them, forming a slurry with them, contacting flue gases with the slurry and disposing of the contaminated slurry. This disclosure relates only to enough of the entire slurry system as will lend understanding to the invention embodied in the measuring and control of the undissolved solids in the slurry.

After the slurry is discharged through line 8 there is a disposal problem of the spent material. One step in the disposal is a reduction of the liquid content at thickener 9. The water which is separated from the solids at this point obviously contains the dissolved solids, or chemical species. It is this water which finds unique use in the measuring system of bubbler 12.

Again, it serves no immediate purpose to disclose details of the thickener unit 9. Whatever structure is used to separate the water and solids of the slurry, the water is made available over weir 10. However made available, the water and dissolved solids are conducted to the measuring system. It is the analysis of the reason for the error in measurement, and the recognition of the solution of the problem with the water available from the thickener unit 9, that brought the invention into being.

BUBBLER SYSTEM 12 OF FIG. 2

The water from weir 10 is flowed to bubbler system 12 through pipe 25. This pipe 25 is connected to dual bubbler pipes 15 and 16 through flow controllers 26 and 27. Essentially, then, pipe 25 is connected to the upper ends of pipes 15 and 16 and the lower ends of the pipes extend downward, below the surface of the slurry in tank 6. Pipe 15 extends down to elevation 28 and pipe 16 extends down to elevation 29. The vertical distance between the lower ends of the pipes is designated H for purposes of analysis.

There are various valves in the piping system which are actuated for shutdown of the system and maintenance. However, these are details which are of no present concern. The basic fact is that a cell 30 is connected to pipes 15 and 16 to respond to the difference in pressure between the fluids in the two pipes. The cell 30 then generates a signal representative of the pressure differential.

There are many available metering and/or control mechanisms which will respond to the differential signal generated by cell 30. In general they are arranged to activate a fluid pressure valve to establish a range of output pressures which can be used to control whatever is appropriate to regulate factors influencing the differential pressure. This mechanism is here represented by a simple box 31 mechanically linked to cell 30. The output control signal of box 31 is carried by pipe 20 to the valve 21. Thereafter, any change of differential pressure sensed by dual bubbler pipes 15 and 16 results in a change density of the slurry to return the differential pressure to the desired value, or set point.

To give analysis to the problem solved by supplying bubbler liquid compatible with slurry liquid, a few elemental mathematics is in order. First, it is stated what may now be apparent from the disclosure. The difference in pressure between elevation 28 and 29 is the same regardless of the variations in the level of slurry in tank 6. Furthermore, the differential pressure will be zero if the density of the bubbler medium is equal to the density of the tank medium, providing the bubbler pipes are full. Since the bubbler uses the weir water return as the bubbler medium, then the density of the bubbler liquid will always be the same as the density of the liquid portion of the slurry. Hence, any density variation of the liquid portion of the slurry will not show up in the differential pressure measurement. The differential pressure readout will, therefore, be only proportional to the density variations that are due to the undissolved solids, or weight percent solids.

With mathematics, a series of statements is now in order:

Case 1 - No Dissolved Solids
$G_1$ = Specific gravity at 0% solids.
$G_2$ = Specific gravity at 15% solids.
$G_b$ = Specific gravity of bubbler medium, $G_b = G_1$ in this case.
$H$ = Difference in elevation (inches).
$DP$ = Differential pressure (inches).
It next follows:
Instrument span $DP = H(G_2 - G_1)$ inches.
Span elevation = $H(G_1 - G_b) = H(G_1 - G_1) = 0$
The full scale calibration, therefore, is,
$0 - 15\%$ solids = $0 - DP$ inches.
Case 2 - Dissolved Solids Present $DG_1$ = Change in specific gravity due to dissolved solids.
$G_3$ = Specific gravity at 0% solids = $G_1 + DG_1$.
$G_4$ = Specific gravity at 15% solids = $G_2 + DG_1$.
$G_b$ = Specific gravity of bubbler medium, $G_b = G_1 + G_1$.

It then follows:
Instrumentation span DP = $H(G_4 - G_3) = H(G_2 + DG_1 - G_1 - DG_1) = H(G_2 - G_1)$.
Span elevation = $H(G_3 - G_b) = H(G_1 + DG_1 - G_1 - DG_1) = 0$
Hence, full scale calibration is maintained and
0 − 15% solids = 0 − DP inches.

To mathematically demonstrate the percent error which would be introduced with only 0.02 S.G.U. change due to dissolved solids, using a prior art water bubbler:

From Case 2 above, density of the water bubbler becomes $G_b = G_1$.
Instrument span $DP = H(G_2 - G_1)$
Span elevation = $H(G_3 - G_b) = H(G_1 + DG_1 - G_1)$
= $H(DG_1)$ inches.

Typical example of the error that would be produced for, $G_2 - G_1 = 0.1$ S.G.U.

$DG_1 = 0.02$ S.G.U.

is, $$\text{Error} = \frac{H(DG_1)}{H(G_2 - G_1)} \times 100\% = \frac{0.02}{0.1} \times 100\% = 20\%$$

Therefore, it becomes even more evident that the present invention is an important method and structure to maintain a percent solids meter and control system compensated for variations in the dissolved species in the liquid portion of a slurry.

From the foregoing, it will be seen that this invention is one well adapted to attain all of the ends and objects hereinabove set forth, together with other advantages which are obvious and inherent to the method and apparatus.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawings is to be interpreted in an illustrative and not in a limiting sense.

The invention, having been described, what is claimed is:

1. A method of manifesting the percent undissolved solids in a mixture of finely divided undissolved solids and liquid with dissolved solids, including, establishing a collection of a mixture of finely divided undissolved solids and a first liquid with dissolved solids, injecting a second liquid with only dissolved solids equivalent to the dissolved solids of the mixture at two different elevations in the collected mixture, sensing the differential between the pressures required to inject the second liquid at the two different elevations, and manifesting the differential pressures as the density of the mixture and percent undissolved solids in the mixture.

2. The method of claim 1, including,
establishing a control signal with the differential pressures,
and applying the control signal to vary the supply of finely divided undissolved solids to maintain the density of the mixture at a predetermined value.

3. The method of claim 2, in which,
the undissolved solids is milled lime/limestone to be used for removing undesirable constituents from combustion gases,
the dissolved solids are chemical species like calcium, sulfate, sulfite and magnesium ions,
and the second liquid is injected in the collected mixture through a dual bubbler pipe system.

4. A control system for the density of a mixture of finely divided undissolved solids and liquids with dissolved solids, including,
a means for combining finely divided undissolved solids and a first liquid with dissolved solids into a mixture,
a tank through which the mixture is passed and in which the mixture is maintained at a predetermined level,
a dual bubbler system with two pipes extended into the mixture within the tank, the open end of each pipe terminating at a different elevation below the surface of the mixture,
a supply of a second liquid with only dissolved solids equivalent to the dissolved solids of the mixture connected to flow the liquid into the bubbler system and discharge from the open ends of each pipe to establish different pressures in each pipe,
a differential pressure cell connected to the two pipes to generate a signal representative of the difference between the pressures of the second liquid in the two pipes,
and means for applying the differential pressure signal to control the means regulating the density of the mixture of undissolved solids and liquid passed through the tank to maintain the mixture at a predetermined density.

5. The system of claim 4 in which,
the undissolved solids are lime/limestone applied to remove undesirable constituents from combustion gases,
the dissolved solids are chemical species like calcium, sulfate, sulfite and magesium ions,
and the supply of second liquid is liquid separated from the undissolved solids of the mixture after the mixture has been flowed from the tank and connected to the bubbler system.

* * * * *